(12) United States Patent
Blomberg et al.

(10) Patent No.: US 8,323,475 B2
(45) Date of Patent: Dec. 4, 2012

(54) APPARATUS AND METHOD FOR ANALYTICAL DETERMINATIONS USING AMPEROMETRIC TECHNIQUES

(75) Inventors: Scott Everett Blomberg, Plymouth, MN (US); James Donald Kurkowski, Roseville, MN (US); Kee Van Sin, Lino Lakes, MN (US)

(73) Assignee: International Technidyne Corporation, Roseville, MN (US)

( * ) Notice: Subject to any disclaimer, the term of this patent is extended or adjusted under 35 U.S.C. 154(b) by 1809 days.

(21) Appl. No.: 10/394,674

(22) Filed: Mar. 20, 2003

(65) Prior Publication Data

US 2004/0182722 A1    Sep. 23, 2004

(51) Int. Cl.
G01N 27/327 (2006.01)
G01N 27/403 (2006.01)

(52) U.S. Cl. .......... 205/792; 204/403.03; 204/406; 204/431

(58) Field of Classification Search .......... 204/400, 204/403.1, 403.03, 403.05, 406, 431; 205/777.5, 205/783, 792
See application file for complete search history.

(56) References Cited

U.S. PATENT DOCUMENTS

| | | | |
|---|---|---|---|
| 4,786,394 A | | 11/1988 | Enzer et al. |
| 5,120,420 A | * | 6/1992 | Nankai et al. ............. 204/403.11 |
| 5,266,179 A | * | 11/1993 | Nankai et al. ............. 204/401 |
| 5,366,609 A | * | 11/1994 | White et al. ............. 204/403.04 |
| 5,405,510 A | | 4/1995 | Betts et al. |
| 5,411,647 A | * | 5/1995 | Johnson et al. ............. 205/777.5 |
| 5,438,271 A | * | 8/1995 | White et al. ............. 324/444 |
| 5,497,772 A | * | 3/1996 | Schulman et al. ............. 600/347 |
| 5,670,031 A | * | 9/1997 | Hintsche et al. ............. 205/777.5 |
| 5,747,666 A | | 5/1998 | Willis |
| 5,821,399 A | | 10/1998 | Zelin |
| 6,037,178 A | | 3/2000 | Leiner et al. |
| 6,193,864 B1 | | 2/2001 | Leader et al. |
| 6,652,720 B1 | * | 11/2003 | Mansouri et al. ............. 204/403.11 |

FOREIGN PATENT DOCUMENTS

| | | |
|---|---|---|
| EP | 1 093 854 A1 | 4/2001 |
| WO | WO 94/09359 | 4/1994 |
| WO | WO 99/17114 | 4/1999 |

OTHER PUBLICATIONS

Bard et al, Electrochemical Methods, $2^{nd}$ Edition, 2001, pp. 640-644.*
Bard and Faulkner, Electrochemical Methods, Fundamentals and Applications, 2nd edition, 2001, pp. 24-28.*
Skoog et al, Principles of Instrumental Analysis, 5th edition, 1998, pp. 661-664.*
Bard, A. et al., "Chapter 13, Electrochemical Instrumentation," *Electrochemical Methods Fundamentals and Applications*, pp. iii and 553-575 (1980).

* cited by examiner

*Primary Examiner* — Kaj K Olsen (57) ABSTRACT

A system for operating at least first and second amperometric sensors includes a cartridge and a control device. The cartridge includes a first amperometric sensor and a second amperometric sensor. The first amperometric sensor is in fluid flow communication with a liquid sample inlet and includes a first electrode. The second amperometric sensor is in fluid flow communication with a liquid sample and includes a second electrode. The control device sets the first and second electrodes to about the same potential such that the first and second amperometric sensors can be operated simultaneously.

28 Claims, 6 Drawing Sheets

APPARATUS AND METHOD FOR ANALYTICAL DETERMINATIONS USING AMPEROMETRIC TECHNIQUES

TECHNICAL FIELD

The present disclosure relates generally to medical diagnostic techniques and equipment. It particularly concerns techniques and equipment for blood analyses. The technology specifically concerns amperometric measurements, for example arrangements for simultaneously making at least two amperometric measurements, such as blood $pO_2$ and glucose measurements. Methods of operation are also provided.

BACKGROUND

In the medical industry, it has become desirable to conduct analytical evaluations using easily handled sample cartridges. In general, the sample cartridges are used with an analytical base station. A liquid sample (typically blood) to be analyzed is put into the sample cartridge. The cartridge is then connected to the analytical base station (or module), for conduct of analytical analyses. In some instances, a calibrant solution or gel is also evaluated. Two commercially available types of analytical base stations for conduct of such analysis, are the IRMA Blood Analysis System (IRMA) and the Blood Analysis Portal system (PORTAL), both of which are available from Diametrics Medical Inc., of Roseville, Minn. 55113, the assignee of the present application.

General features of analytical systems such as IRMA and PORTAL are characterized, for example, in U.S. Pat. No. 6,066,243 ('243), assigned to Diametrics Medical Inc. the complete disclosure for the '243 patent is incorporated herein by reference. Improvements relating to liquid sample cartridges usable with such arrangements are described in: (a) abandoned U.S. application Ser. No. 10/160,329, filed May 30, 2002, and entitled "Cartridge arrangement, Fluid analyzer Arrangement and Methods" (the Thornberg, et al. application), now abandoned; (b) co-pending U.S. application Ser. No. 10/185,201, filed Jun. 28, 2002, entitled "Analytical Test Cartridge, and Methods" (the Kee Van Sin application); and (c) co-pending U.S. application Ser. No. 10/210,661 filed Jul. 31, 2002, and entitled "Apparatus and Method for Hematocrit Determinations" (the Blomberg, et al. application), each of which are currently assigned to the assignee of the present disclosure and are incorporated herein by reference, issued as U.S. Pat. No. 6,794,877.

In general, cartridges characterized in the references of the previous paragraph include various types of sensors therein, for evaluating characteristics of a fluid sample introduced into the cartridge. The sensors may be of various types including, for example, amperometric sensors.

In general, a conventional amperometric sensor includes three electrodes: a working electrode, a reference electrode, and an auxiliary electrode. Amperometric sensors can also include only two electrodes. The circuit is designed such that the potential between the reference electrode and the working electrode is set to a specific value. The value is generally selected for the particular component within the fluid to be analyzed. Under the specific value of the potential between the working and the reference electrode, an electrochemical reaction occurs that generates a current. The circuit causes current to flow to the auxiliary electrode to counter the current being generated by the electrochemical reaction, such that the potential between the working electrode and the reference electrode remains at the specific value and the electrochemical reaction continues.

If two or more amperometric sensors of this type were placed in the same fluid with the sensors operated or polarized simultaneously, current could flow between the sensors, and thus the sensors could interfere with one another. Therefore, improvements are desirable.

SUMMARY

In one aspect of the present disclosure, a system for operating at least first and second amperometric sensors is discussed. The system includes a cartridge and a control device. The cartridge includes a first amperometric sensor and a second amperometric sensor. The first amperometric sensor is in fluid flow communication with a liquid sample inlet and includes a first electrode. The second amperometric sensor is in fluid flow communication with a liquid sample and includes a second electrode. The control device sets the first and second electrodes to about the same potential such that the first and second amperometric sensors can be operated simultaneously.

In another aspect of the present disclosure, a method of simultaneously operating at least first and second amperometric sensors is discussed. The method includes providing a first amperometric sensor in fluid flow communication with a liquid sample inlet and includes a first electrode; providing a second amperometric sensor in fluid flow communication with the liquid sample inlet and includes a second electrode; and setting the first and second electrodes to about the same potential such that the first and second amperometric sensors can be operated simultaneously.

In another aspect of the present disclosure, a method of operating first and second amperometric sensors is discussed. The method includes setting a goal fluid potential value; reading a first electrode potential within the first amperometric sensor; reading a second electrode potential within the second amperometric sensor; and calculating an adjustment to the first and second electrode potentials such that the first and second sensor can be operated simultaneously.

In another aspect of the present disclosure, a cartridge for analyzing at least first and second analytes is discussed. The cartridge includes first and second amperometric sensors. The first amperometric sensor is in fluid flow communication with a liquid sample inlet and includes a first electrode and a first sensor membrane positioned between the first electrode and a fluid flow channel. The second amperometric sensor is in fluid flow communication with the liquid sample inlet and includes a second electrode and a second sensor membrane positioned between the second electrode and the fluid flow channel. The first and second sensor membranes are configured to have a high impedance such that the first and second amperometric sensors can be simultaneously operated.

A more complete appreciation of the present invention and its scope may be obtained from the accompanying drawings, that are briefly described below, from the following detailed descriptions of presently preferred embodiments of the invention and from the appended claims.

DETAILED DESCRIPTION

This disclosure generally includes techniques for improved amperometric sensor arrangements and operation that can be readily incorporated, for example, into analytical sample cartridges for medical use. Sample cartridges of this type preferably have an area of no greater then 100 square cm, typically no larger then 80 square cm, and are usually of a size of about 50 square cm or smaller. Typically, such cartridges are no more then 3 cm high (discounting any attached syringe). Generally each includes a sample fluid injection port, various sensors for conduct of analytical analyses of liquid samples such as blood injected into the injection port; various electrical leads for communication with electronic equipment within an analytical module base station for control of analytical testing and communicating data and/or results; and, various mechanical structure to facilitate mounting or removal of the cartridge with respect to the analytical equipment.

In general, such analytical cartridges have relatively short useful lifetimes, with respect to the lifetime of the analytical componentry with which they are used. As a result, such cartridges are sometimes referred to as "disposable cartridges" or "disposable test cartridges." Indeed, in many instances, the cartridges are single use cartridges.

Figure 1:
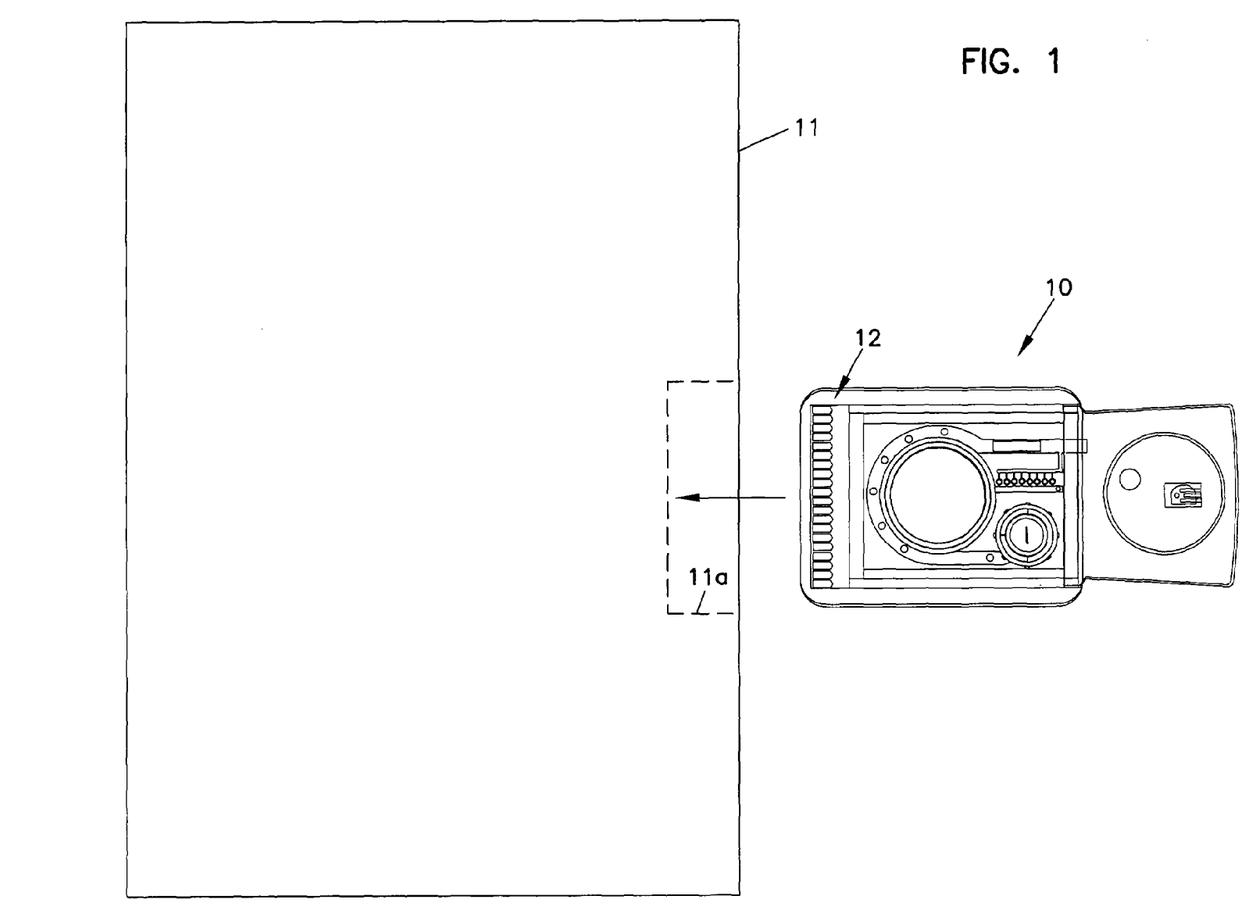
FIG. 1 is a schematic diagram of an analytical cartridge according to the present disclosure shown being inserted into an analytical base station, for use.

Referring to FIG. 1, an analytical cartridge 10 is depicted being inserted into an analytical base station 11, at receiver 11a, for use. Of course, the analytical base station 11 can be portable. By the term "portable," it is meant that the system, without the power supply, can be carried by one person and weighs no more than 15 pounds.

In general, the analytical cartridge 10 would include a liquid sample to be analyzed, for example a blood sample and/or a calibrant; and the analytical base station 11 would include an appropriate central processing unit or capability to control and direct evaluations made within the cartridge, to manage electrical output from the cartridge, and to provide or direct any necessary calculations or communications regarding that data.

In general, when the cartridge 10 is inserted into the analytical base station 11, electrical termini 12 come into appropriate electrical connection with appropriate portions with the analytical base equipment 11 for operation. The analytical base station 11, for example, can comprise an IRMA system or PORTAL system, as identified above, with appropriate programming to control and assess the particular analytical evaluations conducted with the cartridge 10.

Figure 2:
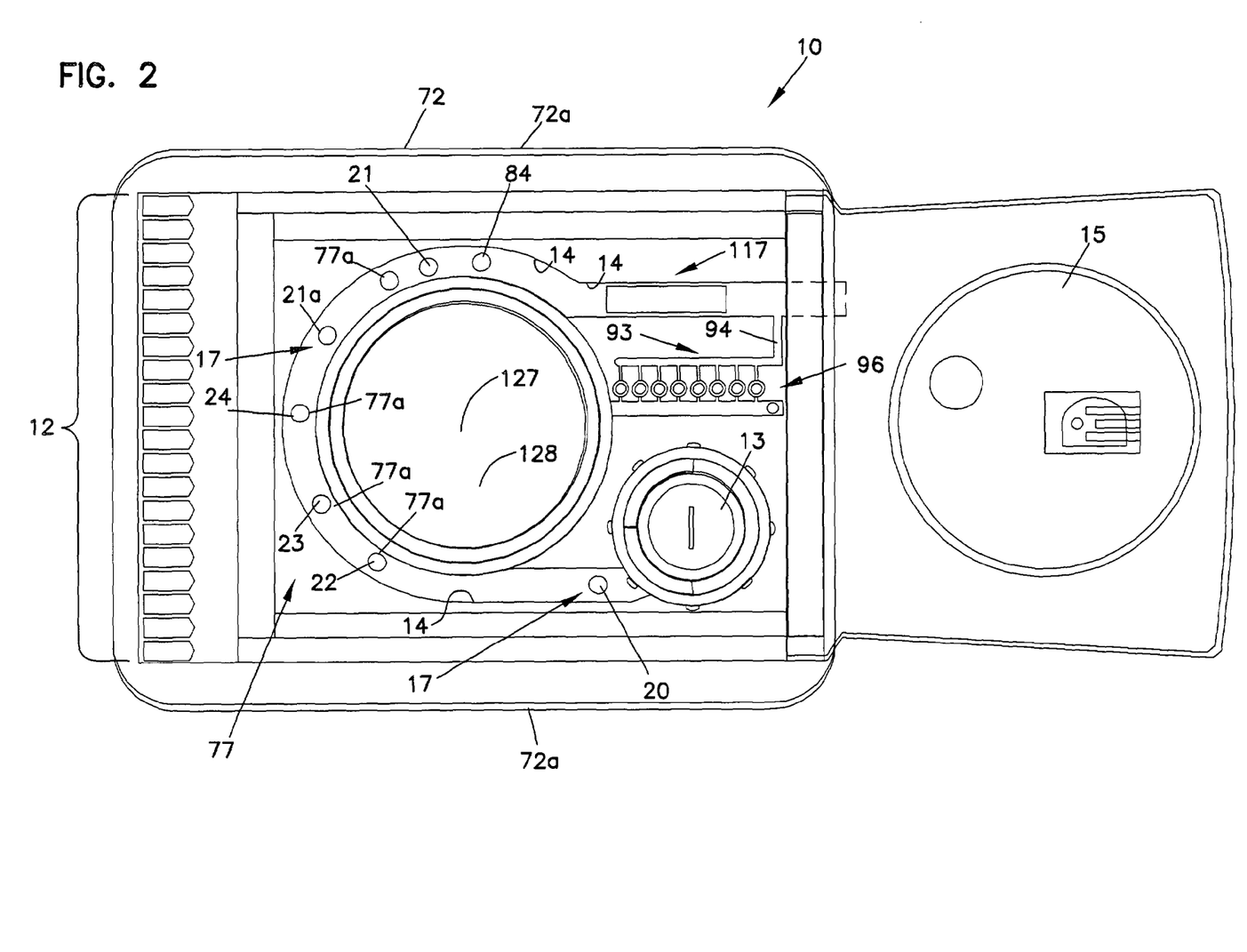
FIG. 2 is a schematic diagram of an analytical cartridge including multiple amperometric sensors, usable for conducting analytical evaluation, of a selected fluid sample, in accord with a present disclosure.

Referring to FIG. 2, analytical cartridge 10 is depicted (schematically). Cartridge 10 includes a sample injection port 13 into which a liquid sample to be evaluated can be inserted. It is anticipated that for many uses the sample will be initially contained in a syringe, in which case the inlet port 13 can be provided with a Luer-Lock or other lock or syringe engagement structure, to facilitate engagement with a syringe for fluid transfer from the syringe into the cartridge 10 without spillage.

The cartridge 10 includes and defines a flow channel or chamber 14. In this instance, the flow chamber 14 is in communication with, and extends between, the inlet 13 and an opposite fluid terminus or reservoir 15.

Within the fluid flow channel or chamber 14 is positioned a multiple amperometric sensor arrangement or system 17. In this instance, the multiple amperometric sensor system 17 comprise at least two simultaneously operable amperometric sensors, namely a first amperometric sensor 20 and a second amperometric sensor 21. An optional third amperometric sensor 21a. is also depicted. Other additional amperometric sensors could also be included.

Before additional features relating to the cartridge 10, FIG. 2, are discussed, the multiple amperometric sensor system 17 will be discussed in detail.

Multiple Amperometric Sensor System

Figure 3:
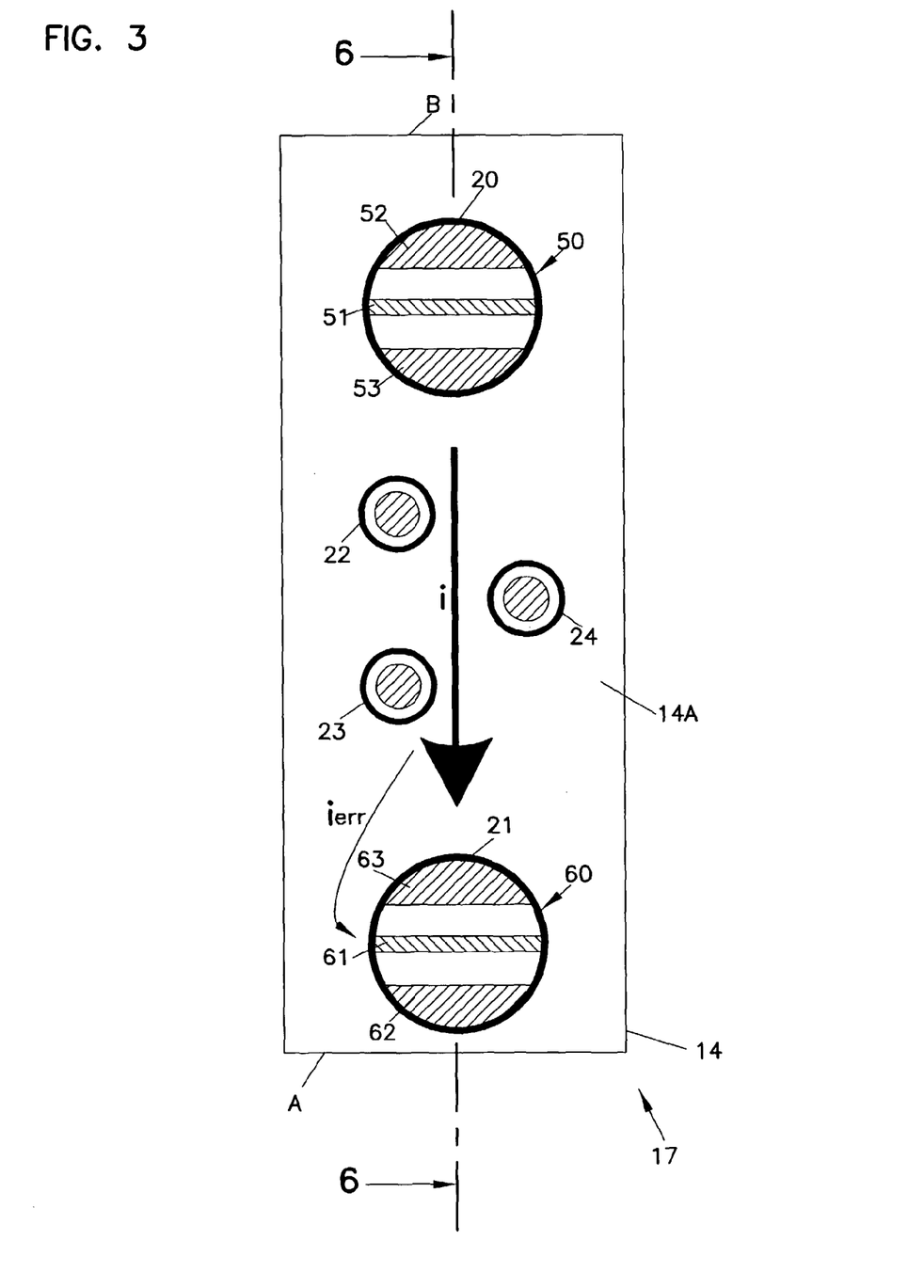
FIG. 3 is an enlarged schematic depiction of first and second amperometric sensors in a single flow path in the arrangement depicted in FIG. 2.

Attention is now directed to FIG. 3., which is an enlarged, fragmentary, schematic description of the portion of flow channel 14 having the multiple amperometric sensor system 17 therein. First amperometric sensor 20 and second amperometric sensor 21 are viewable. Positioned between sensors 20 and 21 are shown three non-amperometric sensors 22, 23, and 24. By the term "non-amperometric sensor" or variants thereof, in this context, reference is meant to an analytical sensor that is operated other than through an amperometric approach. Of course there is no requirement that there be any sensor of any type, positioned between the first and second amperometric sensors 20, 21. The arrangement indicated in FIG. 3 is merely meant to be an example. It is noted that the multiple amperometric sensor system 17 may include more than two amperometric sensors therein, and thus optional third amperometric sensor 21a is depicted in FIG. 2. In this part of the discussion, however, only the first and second amperometric sensors 20, 21 of a multiple amperometric sensor system 17 are described in detail.

Attention is first directed to the first amperometric sensor 20. The first amperometric sensor 20 is a three electrode sensor 50, comprising a first working electrode 51, a first reference electrode 52, and a first auxiliary (or counter) electrode 53. Of course, the first amperometric sensor could involve only two electrodes.

In general, the first amperometric sensor 20 is constructed and arranged for an amperometric evaluation conducted on a liquid sample positioned in flow channel 14. The analyte ($A_1$) to be evaluated by the first amperometric sensor 20 could be a variety of materials. For example, the particular analyte ($A_1$) for the first amperometric sensor 20 could be $O_2$. That is, the first amperometric sensor 20 could be a $pO_2$ sensor. Other examples of analyte are glucose, lactate, creatinine, and creatine.

In general, for conventional amperometric evaluations, a potential is established between the reference electrode, for example, first reference electrode 52, and the working electrode, for example, first working electrode 51, selected to correspond with an analytical potential for the analyte ($A_1$) at which an electrochemical and current generating reaction occurs. For a $pO_2$ sensor, this would typically be at about +700 millivolts between the working electrode and the reference electrode. The potential of the auxiliary electrode, for example, first auxiliary electrode 53, would have a current driven by the circuit in proportion to the current flowing as a result of the electrochemical reaction, such that the potential between the working electrode and the reference electrode remains constant at about +700 millivolts. The measured current is proportional to oxygen presence, and can be correlated to a $pO_2$ value. This current B is preferably not greater than 500 nA and typically not greater 100 nA. It is noted that the first amperometric sensor 20 could be operated in this conventional manner, if desired. However, preferably the arrangement is operated in a different manner as described below, so that the first and second amperometric sensors 20, 21 can be operated simultaneously, without interference with one another. This will be understood from further description.

Still referring to FIG. 3, the second amperometric sensor 21 is also a three electrode sensor 60, including a second working electrode 61, a second reference electrode 62 and a second auxiliary electrode 63. Of course, the second amperometric sensor could also include only two electrodes. The three electrode sensor 60 is generally configured for evaluation of a second analyte ($A_2$), for example glucose. An amperometric sensor 21 for glucose is typically set at a potential of −700 millivolts between the second working electrode 61 and the second reference electrode 62.

Referring to FIG. 3, a segment 14a of the fluid flow channel 14, in which the multiple amperometric sensor arrangement 17 (i.e., first and second amperometric sensors 20, 21) is positioned, is generally referred to herein as the "amperometric sensor flow channel segment." This segment generally extends between points A and B, i.e., between opposite edges of the first and second amperometric sensors 20, 21. In a typical embodiment, the first and second amperometric sensors 20, 21 will be positioned, along the segment 14a with a distance of no greater than 2 cm and typically no greater than 1 cm, apart from one another. This arrangement of electrodes is such that the auxiliary potential is important to the solution. Many different electrode configurations are possible and FIG. 3 is just one example configuration.

From the above, it will be apparent that if the first amperometric sensor 20 and the second amperometric sensor 21 are operated simultaneously in the manner described for a conventional amperometric sensor, the two would interfere with one another. Specifically, current would tend to flow from the first amperometric sensor 20 to the second amperometric sensor 21 through the flow channel 14a, given the different potentials described above. Of course, the two amperometric sensors 20, 21 could each be operated in a conventional manner, but not simultaneously. Problems with this concern the fact that in time, blood characteristics could change; and, it is also desirable that the analytical evaluations be conducted in as short a period of time as possible, preferably no more than about 2 minutes.

In general, the present disclosure concerns configuring and operating the multiple amperometric sensor system 17 such that the various sensors therein, for example the first amperometric sensor 20 and the second amperometric sensor 21 can be simultaneously operated without interference with one another. In general, the first auxiliary electrode 53 and the second auxiliary electrode 63 are configured to be maintained at about the same voltage, relative to ground, so that no current will flow through the communication channel 14a between the first amperometric sensor 20 and the second amperometric sensor 21. By the term "about the same voltage," unless otherwise stated, it is meant that voltages are within plus or minus 10 millivolts of each other. The system described herein typically has a current flow between the first amperometric sensor 20 and the second amperometric sensor 21 of less than 1 nA, and preferably less than 0.4 nA.

In order to maintain specific voltages between the working electrodes 51, 61 and the corresponding reference electrodes 52, 62, such that an electrochemical reaction still occurs, as described above, the first and second working electrodes 51, 61 and first and second reference electrodes 52, 62 are varied by digital to analog converters, as will be described in more detail below. For a particular sensor, the potential drop between the reference and working electrodes (or bias potential) is kept fixed. This adjustment of the potentials (relative to the instrument ground) allows for the potential imparted upon the sample to be adjusted. In addition, the potential of each auxiliary electrode is measured directly by an analog to digital converter.

Since the test is dynamic and signals can change on a second by second basis, the potential of the auxiliary electrodes (relative to ground) are adjusted each second. The auxiliary electrode potentials are measured and stored by the microprocessor. The values of these potentials are compared. Then at least one set of reference and working electrode potentials are adjusted by the microprocessor such that the potentials of all the auxiliary electrodes will match each other to the same goal potential.

The result is no potential drop between the auxiliary electrodes and, as a result, no potential difference will be imparted on the fluid sample by the amperometric sensors. Therefore, no current will flow between them. Since no current will be flowing between them, the sensors will not interfere with one another. Since the working to reference electrode potential will maintain constant, there will be no change in the output signal.

Figure 4:
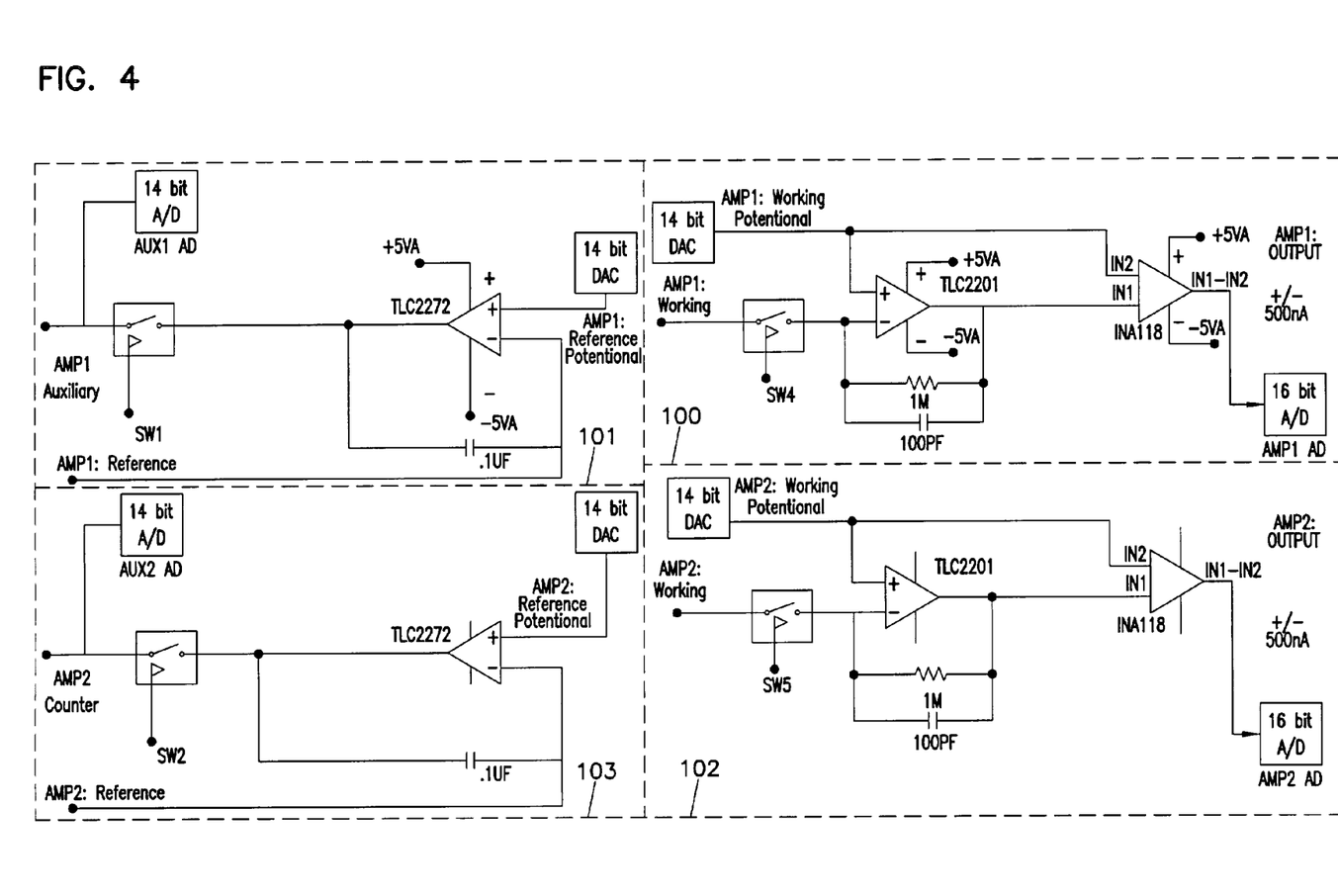
FIG. 4 is a circuit diagram for the first and second amperometric sensors depicted in FIG. 3.

FIG. 4 is an electrical schematic of the multiple amperometric system 17 described above. FIG. 4 illustrates the use of a combination of digital and analog electronics. One skilled in the art will readily recognize that the multiple amperometric system 17 could be configured using all digital circuitry, all analog circuitry, or different combinations of digital and analog circuitry than that shown in FIG. 4 to achieve the desired results described above.

In general the system 17 includes circuitry for the first working electrode 51, designated by the dashed box 100; the first auxiliary electrode 53 and first reference electrode 52, designated by the dashed box 101, the second working electrode 61, designated by the dashed box 102; and the second auxiliary electrode 63 and second reference electrode 62, designated by the dashed box 103. This circuitry is used by a microprocessor (not shown) to vary and control the potentials of each electrode 51, 52, 53, 61, 62, 63 as described above.

Figure 5:
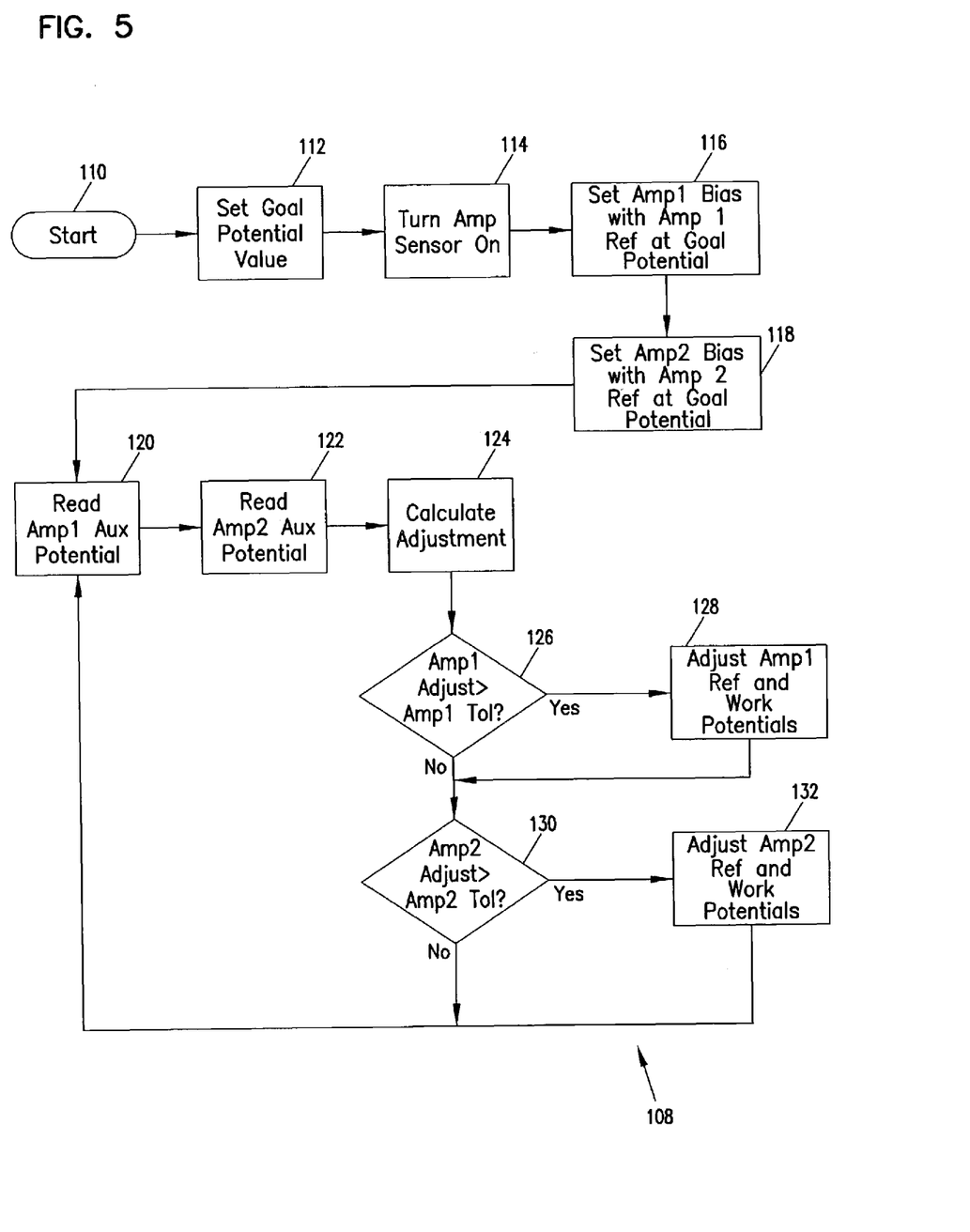
FIG. 5 is a logic flow diagram for the first and second amperometric sensors depicted in FIG. 3.

FIG. 5 is a flow chart depicting a system 108 used by the microprocessor to vary and control the potentials of each electrode, for example the electrodes 51, 52, 53, 61, 62, 63 described above. The logic flow begins at start block 110. A goal module 112 sets the goal potential value for the amperometric sensors, for example, the first and second amperometric sensors 20, 21. An on module 114 turns on the amperometric sensors. A first bias module 116 sets the potential between a first working electrode and a first reference electrode. A second bias module 118 sets the potential between a second working electrode and a second reference electrode.

A first read module 120 reads a first auxiliary potential. A second read module 122 reads a second auxiliary potential. A calculate module 124 calculates an adjustment to the electrodes such that the potential between the working and the reference electrodes remains substantially constant. A first decision operation 126 determines if the needed adjustment for the first amperometric sensor is greater than the tolerance allowed for the first amperometric sensor. If the first decision operation 126 determines that the needed adjustment is greater than the tolerance for the first amperometric sensor, then the logic branches YES to a first adjust module 128. The first adjust module 128 adjusts the first working potential and the first reference potential.

A second decision operation 130 determines if the needed adjustment for the second amperometric sensor is greater than the tolerance allowed for the second amperometric sensor. If the second decision operation 130 determines that the needed adjustment is greater than the tolerance for the second amperometric sensor, then the logic branches YES to a second adjust module 132. The second adjust module 132 adjusts the second working potential and the second reference potential.

Referring back to the first decision operation 126, if the first decision operation 126 determines that the needed adjustment is not greater than the tolerance for the first amperometric sensor, then the logic branches NO to the second decision operation 130 and flow continues as described above. If the second decision operation 130 determines that the needed adjustment is not greater than the tolerance for the second amperometric sensor, then the logic branches NO to the first read module 120 and flow continues as described above.

The above described system 108 can best be understood in terms of an example. Referring to FIGS. 3 and 5, logic flow begins at start block 110. The goal module sets the goal potential for the first amperometric sensor 20 to 700 millivolts and the goal potential for the second amperometric sensor 21 to −700 millivolts. The on module 114 turns on the first and second amperometric sensors 20, 21. The first bias module 116 sets the first working electrode 51 and the first reference electrode 52 to a 700 millivolts potential between them. The second bias module 118 sets the second working electrode 61 and the second reference electrode 62 to a−700 millivolts potential between them.

A first read module 120 reads the potential of the first auxiliary electrode 53. The second read module 122 reads the potential of the second auxiliary electrode 62. The calculate module 124 calculates a first needed adjustment for the first working and first reference electrodes 51, 52 such that the potential between them remains at 700 millivolts. The calculate module 124 also calculates a second needed adjustment for the second working and second reference electrodes 61, 62 such that the potential between them remains at −700 millivolts.

In one implementation, a method of operating at least first and second amperometric sensors may be employed that includes setting a goal fluid potential value, reading a first electrode potential within the first amperometric sensor, reading a second electrode potential within the second amperometric sensor; and calculating an adjustment to the first and second electrode potentials, such that the first and second amperometric sensors can be operated simultaneously. Reading the first electrode potential includes reading a first auxiliary potential, and reading a second electrode potential includes reading a second auxiliary potential. Alternatively, reading a first electrode potential can include reading a first working potential, and reading a second electrode potential can include reading a second working potential. In addition, reading a first electrode potential can include reading a first reference potential, and reading a second electrode potential includes reading a second reference potential.

In this example, the first decision operation 126 determines that the first needed adjustment is greater than a first tolerance for the first amperometric sensor 20, and the flow branches YES to the first adjust module 128. The first adjust module 128 adjusts the first working and reference electrodes 51, 52 accordingly. In this example, the second decision operation 130 determines that the second needed adjustment is greater than a second tolerance for the second amperometric sensor 21, and the flow branches YES to the second adjust module 132. The second adjust module 130 adjusts the second working and reference electrodes 61, 62 accordingly. Logic flow branches to the first read module 120, and the flow continues as described above.

In another example, the logic flow continues as described above until it reaches the first decision operation 126. In this example, the first decision operation 126 determines that the first needed adjustment is not greater than the first tolerance for the first amperometric sensor 20, and flow branches NO to the second decision operation 130. In this example, the second decision operation 130 determines that the second needed adjustment is not greater than the second tolerance for the second amperometric sensor 21, and flow branches NO to the first read module 120, and flow continues as described above.

A multiple amperometric sensor system 17, as generally discussed above in connection with FIGS. 1-5, can be incorporated into a cartridge 10 that is dedicated to amperometric sensor measurements, i.e. which does not allow for measurement of any liquid parameter (blood characteristic) other than through the sensors (for example sensors 20, 21) of the multiple amperometric sensor system 17. In other arrangements, the multiple amperometric sensor system 17 may be positioned within a cartridge 10 which is configured for measuring other liquid sample characteristics. Such an arrangement is depicted in FIG. 2.

Referring again to FIG. 2, cartridge 10 generally includes a base structure 72 including mounting structure or flanges 72a facilitate mounting on analytical base equipment for use.

The cartridge 10 further includes an analytical sensor arrangement 77, comprising auxiliary sensors 77a and a counter or reference electrode 84. It should be noted that for the particular cartridge 10 depicted, three of the sensors 77a, namely sensors 22, 23 and 24, are positioned between amperometric sensors 20 and 21. This is to indicate a possible manner in which the arrangement can be configured. It is noted that there is no requirement that the sensors 20 and 21 have other types of sensors positioned between them. It is also noted that spacing sensors 20 and 21 as far apart as possible, is not required given that control of current between them is managed in an alternate manner.

The number and type of sensors 77a may be varied, and is a matter of choice, depending upon the types and number of analyses to be conducted. In general terms, the sensors 77a can be selected from electrical, electrochemical, enzymatic, optical and mechanical sensors. Descriptions related to this are provided, for example, in the Thornberg et. al application, the Kee Van Sin application and the Blomberg application referred to above.

As an example, the sensors 77a can be chosen to determine: creatinine content, blood urea nitrogen (BUN) content, sodium ($Na^+$) content, acidity (pH), carbon dioxide ($pCO_2$) content, calcium ($Ca^{+2}$) content, potassium ($K^+$) content, chloride ($Cl^-$) content, or lactate content, or to conduct coagulation evaluations or to other measure parameters.

Cartridge 10 includes a plurality of electrical termini 12 some of which are in electrical communication with traces, not shown, that communicate with the multiple amperometric sensor arrangement 17, for control of amperometric testing conducted with the sensors 20, 21. In general, selected ones of the electrical termini 12 and any electrically conductive traces which provide such communication, will generally be referred to herein as the multiple amperometric sensor system conductive arrangement leads or channels.

Other ones of the electrical termini 12 are selected to provide communication with traces, not shown, that communicate with the analytical sensor arrangement 77, for control of the sensors 77a. In general, selected ones of electrical termini 12 and any electrically conductive traces that provide such communication, will be generally referred to herein as the auxiliary sensor electrically conductive arrangement, leads or channels.

Still referring to FIG. 2, the cartridge 10 depicted also includes an analytical spur arrangement 93, comprising a second flow channel 94 (in fluid flow communication with channel 14) and plurality (eight being shown) of analytical cells 96, configured for conduct, if desired, of a titration experiment as described the Kee Van Sin application previously incorporated here and by reference. Of course, appropriate ones of termini 12 would be in electrical communication with traces (not shown) and the analytical spur arrangement 93 for conducting such tests. Such electrical termini 12 and associated electrically conductive traces, will be generally referred to herein as the titration cell electrically conductive arrangement, leads or channels.

Further, cartridge 10 includes a hematocrit measurement arrangement 117, for hematocrit testing in accord with the Blomberg et al application. In general, selected ones of the electrical termini 12 and any electrical conductive traces that provide such communication, will generally be referred to herein the hematocrit measurement electrically conductive arrangement, leads or channels.

Of course, the various termini 12 are positioned for contact with the analytical equipment or modules, for operation. Such an arrangement, again, is indicated schematically in FIG. 1.

In general, the sensors 77a, 84 may be of a variety of types. One can use, for example, conventional sensors selected from: ion selective electrodes (potentiometric) sensors; conductometric sensors; and, enzymatic sensors. If the fluid sample is blood, for the sensors 77a in the flow channel 13 (not part of the hematocrit sensor arrangement 11) and not part of the multiple amperometric sensor arrangement 17) typically usable sensors include ion selective electrode sensors to measure pH and $pCO_2$, as well as sodium ($Na^+$), calcium ($Ca^{+2}$), potassium ($K^+$) and chloride ($Cl^{31}$). Blood urea nitrogen (BUN) and creatinine are typically measured using enzymatic sensors. Measurements of blood coagulation would typically be conducted using conductometric sensors.

A titration experiment provided in the analytical cells 96, could for example, be a heparin titration; in which each cell, for example, includes a heparin sensor and a selected amount of titration agent for heparin. As described in the Kee Van Sin application, such a titration could be conducted using an ion selective sensor for heparin, and a titration agent such as protamine.

In some instances, it may be desirable to store certain types of sensors in contact with solution (wet stored), or separate from solution ("dry-stored"). Also it may be desirable to injecting into the channel 14 the blood sample and a calibration sample, at different times. Techniques for creating selected fluid flow or location, and valves to control fluid flow, are described in the Thomberg et al application. In that application, utilization of region 127, FIG. 2 herein, as a calibrant reservoir 128, is described.

A typical cartridge 10 comprises a multicomponent structure including: a base structure or housing; and, an enclosed analytical substrate. The housing would typically comprise molded plastic components, for example polycarbonate components. The analytical substrate would typically comprise a ceramic substrate having deposited thereon: appropriate electrically conductive materials for formation of the sensors and electrical traces; and, any needed chemical or enzyme materials, for operation of the various sensors and cells. The typical cartridge would comprise snap together components, or adhesively secured components. Dimensions for a cartridge would typically be no more than 100 sq. cm. and usually no more than 80 sq. cm., for example 50 sq. cm. or less, as a cartridge perimeter footprint area, with a total height (not including an injection syringe) of typically no greater than about 3 cm. The molded plastic components would include appropriate molded passages or vanes to define the various internal structure such as flow channels, spurs and cells.

A typical cartridge would be configured to hold, during operation, a total unknown fluid (blood) sample volume of no greater than 3 milliliters (ml), typically no more than 200 microliters (μl). The total sample volume extending between the sensors 20 and 21, for a typical experiment, would no more than 3 ml and usually at least 125 ml; most typically about 0.030 ml to 0.250 ml. The calibrant volume in reservoir 128 would typically be about 500 ml. The calibrant would typically comprise an aqueous solution with fixed and known concentrations of at least some of the measured analytes.

Of course, other techniques can also be used to simultaneously operate at least two amperometric sensors, such as the first and second amperometric sensors 20, 21, without interference with one another. In general, another such technique includes increasing the relative impedance of the sensor membranes with respect to the fluid that is being analyzed such that no current will flow through the fluid being analyzed. The impedance of the sensor membranes can be increased by constructing the membranes of low conductivity materials, such as silicone, or by increasing the thickness of the membranes. The interfering current is directly proportional to the potential drop between the sensors and is inversely proportional to the membrane impedances of the sensors. Preferably, the impedance of the sensor membranes is between 1 mega ohm and 100 mega ohms.

Figure 6:
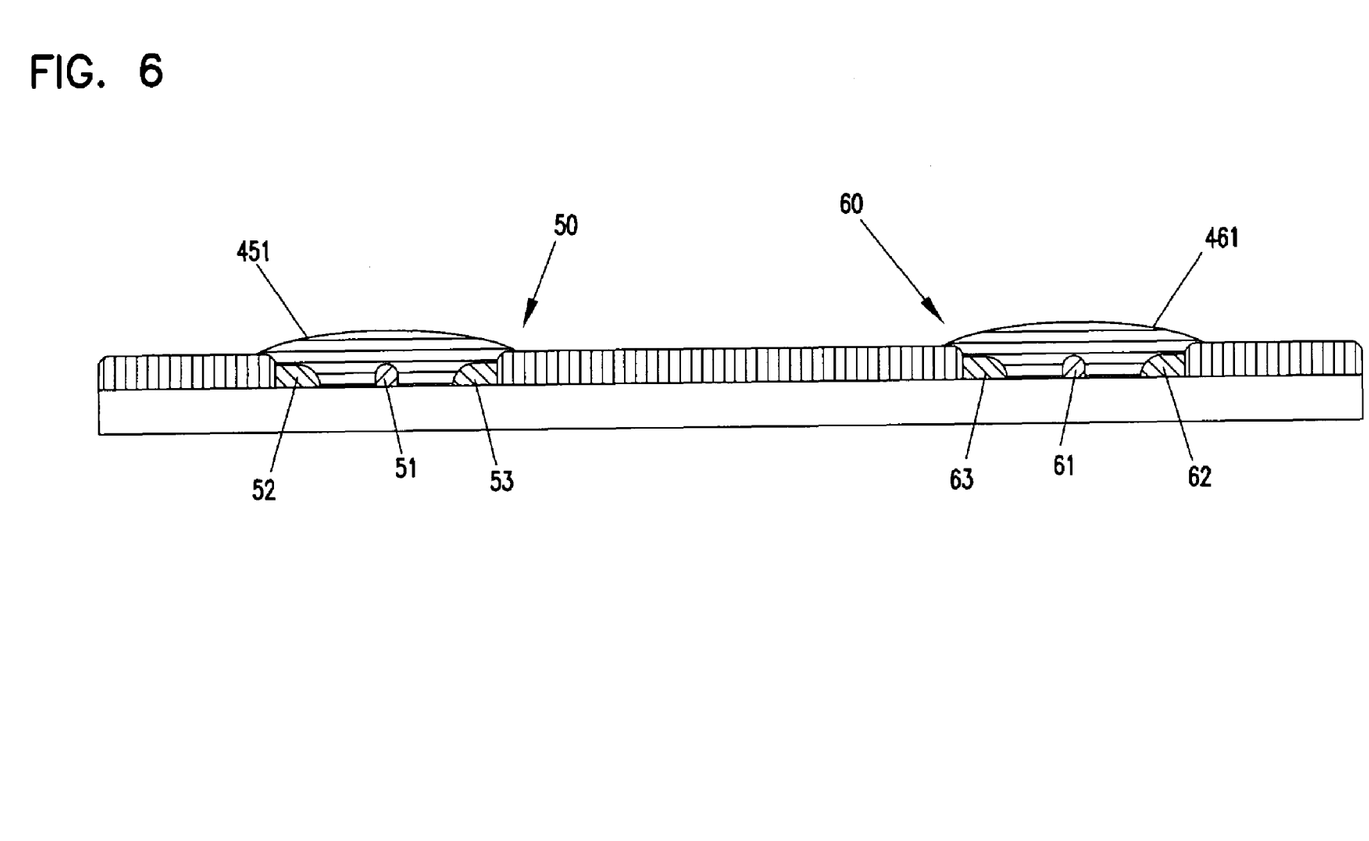
FIG. 6 is a cross-sectional diagram taken along lines 6-6 of the arrangement depicted in FIG. 3.

Referring now to FIGS. 3 and 6, the first amperometric sensor 50 includes a first sensor membrane 451. The second amperometric sensor 60 includes a second sensor membrane 461. The sensor membranes 451, 461 are constructed of a particular low conductivity material and are placed between the sensor electrodes 51, 52, 53, 61, 62, 63 and the fluid being analyzed and cover the sensor electrodes 51, 52, 53, 61, 62, 63.

The sensor membranes 451, 461 serve two primary functions. In the case of the first sensor 50, such as an oxygen sensor, the first sensor membrane 451 acts as a barrier that allows oxygen through but does not allow other substances such as proteins to get to the working electrode 51. These substances could create their own chemical reactions that could result in current flowing into the working electrode 51 and thus interfering with the measurement of oxygen. In the case of the second sensor 60, such as a glucose sensor, the second sensor membrane 461 also contains a substance that reacts with the sample producing another material that is then measured by the second sensor 60.

In general, a particular sensor membrane can be configured for the measurement of the particular analyte that the sensor is measuring. By the term "configured", it is meant that the sensor membrane can be constructed of a particular material having a low conductivity or can be constructed in such a way, for example by increasing the thickness, such that the impedance of the membrane is increased. When the membrane is configured with a high impedance, it is possible to place at least two amperometric sensors 50, 60 in the same fluid flow path 14 and not have them interfere with one another.

The above specification examples and data provide a complete description of the use and principles of the invention. Alternate embodiments of the invention can be made without departing from the spirit and scope of this disclosure.

What is claimed is:

1. A system for operating at least first and a second amperometric sensors, the system comprising:
    (a) a cartridge including:
        (i) a first amperometric sensor in fluid flow communication with a liquid sample inlet and including a first electrode;
        (ii) a second amperometric sensor in fluid flow communication with the liquid sample inlet and including a second electrode; and
    (b) a control device for automatically adjusting voltage to the first and second sensor during testing of a sample so that the first and second electrodes are set to about the same potential such that the first and second amperometric sensors can be operated simultaneously.

2. A system according to claim 1 wherein:
    (a) the first amperometric sensor is a three electrode sensor; and
    (b) the second amperometric sensor is a three electrode sensor.

3. A system according to claim 2 wherein the first electrode is covered by a first membrane having a relatively high impedance, and the second electrode is covered by a second membrane having a relatively high impedance.

4. A system according to claim 1 wherein:
    (a) the first electrode is a first auxiliary electrode; and
    (b) the second electrode is a second auxiliary electrode.

5. A system according to claim 1 wherein:
    (a) the first amperometric sensor is positioned no more than 2 cm from the second amperometric sensor.

6. A system according to claim 1 wherein:
    (a) the first amperometric sensor is an $O_2$ sensor.

7. A system according to claim 1 wherein:
    (a) the second amperometric sensor is a glucose sensor.

8. A system according to claim 1 wherein:
    (a) the cartridge has a perimeter area of no greater than 80 sq. cm.

9. A system according to claim 1 wherein:
    (a) the first and second amperometric sensor are positioned in a flow channel segment having a volume of not greater than 0.250 ml.

10. A system according to claim 1 further including:
    (a) at least one ion selective electrode positioned in the flow channel segment between the first and second amperometric sensors.

11. A system according to claim 1 wherein the cartridge further includes:
    (a) a third amperometric sensor in fluid flow communication with the liquid sample inlet and including a third electrode.

12. A system according to claim 1 wherein the cartridge and control system are portable.

13. A method of simultaneously operating at least first and second amperometric sensors, the method comprising:
    (a) providing a first amperometric sensor in fluid flow communication with a liquid sample inlet and including a first electrode;
    (b) providing a second amperometric sensor in fluid flow communication with the liquid sample inlet and including a second electrode; and
    (c) automatically adjusting the first and second electrodes to about the same potential during testing of a liquid sample provided through the liquid sample inlet, such that the first and second amperometric sensors can be operated simultaneously.

14. A method according to claim 13 wherein:
    (a) providing a first amperometric sensor includes providing a first amperometric sensor having three electrodes; and
    (b) providing a second amperometric sensor includes providing a second amperometric sensor having three electrodes.

15. A method according to claim 13 wherein:
    (a) providing a first amperometric sensor includes providing a first amperometric sensor in fluid flow communication with a liquid sample inlet and including a first auxiliary electrode; and
    (b) providing a second amperometric sensor includes providing a second amperometric sensor in fluid flow communication with a liquid sample inlet and including a second auxiliary electrode.

16. A method according to claim 13 wherein:
    (a) providing a second amperometric sensor includes providing a second amperometric sensor position no more than 2 cm from the first amperometric sensor.

17. A method according to claim 13 wherein:
    (a) providing a first amperometric sensor includes providing an $O_2$ sensor.

18. A method according to claim 13 wherein:
    (a) providing a second amperometric sensor includes providing a glucose sensor.

19. A method according to claim 13 wherein:
    (a) providing first and second amperometric sensor includes providing the first and second amperometric sensor positioned in a flow channel segment having a volume of not greater than 0.250 ml.

20. A method according to claim 13 further including:
    (a) providing at least one ion selective electrode positioned in a flow channel segment between the first and second amperometric sensors.

21. A method according to claim 13 further including:
    (a) providing a third amperometric sensor in fluid flow communication with the liquid sample inlet and including a third electrode.

22. A method of operating at least first and second amperometric sensors, the method comprising:
    (a) setting a goal fluid potential value between electrodes in contact with a fluid sample;
    (b) reading a first electrode potential within the first amperometric sensor;
    (c) reading a second electrode potential within the second amperometric sensor; and
    (d) performing an automatic adjustment to the first and second electrode potentials during testing of the fluid sample that is in contact with the first and second amperometric sensors, to substantially maintain the goal fluid potential value between the first and second electrodes, such that the first and second amperometric sensors can be operated simultaneously.

23. A method according to claim 22 wherein:
    (a) reading a first electrode potential includes reading a first auxiliary potential; and
    (b) reading a second electrode potential includes reading a second auxiliary potential.

24. A method according to claim 22 wherein:
    (a) reading a first electrode potential includes reading a first working potential; and
    (b) reading a second electrode potential includes reading a second working potential.

25. A method according to claim 22 wherein:
(a) reading a first electrode potential includes reading a first reference potential; and
(b) reading a second electrode potential includes reading a second reference potential.

26. A method according to claim 22 further including:
(a) reading a third electrode potential within a third amperometric sensor.

27. A method according to claim 26 further including:
(a) calculating an adjustment to the third electrode potential, such that the first, second, and third amperometric sensors can be operated simultaneously.

28. A method according to claim 27 further including:
(a) adjusting the first, second, and third electrode potentials such that the first, second, an third amperometric sensors can be operated simultaneously.

* * * * *